United States Patent [19]
Olsen et al.

[11] Patent Number: 6,004,747
[45] Date of Patent: Dec. 21, 1999

[54] SALMONELLA IDENTIFICATION BY THE POLYMERASE CHAIN REACTION

[75] Inventors: John Elmerdahl Olsen, Elmekrogen 4, DK-3500 Vaerlos; Soren Aabo, Tokkerupvej 11, Tokkerup, DK-4320 Lejre; Lone Rossen, Roskilde; Ole Feldballe Rasmussen, Maaloev, all of Denmark

[73] Assignees: John Elmerdahl Olsen, Vaerlos; Bioteknologisk Institut, Lyngby; Soren Aabo, Lejre, all of Denmark

[21] Appl. No.: 08/564,110

[22] PCT Filed: Jun. 17, 1994

[86] PCT No.: PCT/GB94/01316

§ 371 Date: Mar. 11, 1996

§ 102(e) Date: Mar. 11, 1996

[87] PCT Pub. No.: WO95/00664

PCT Pub. Date: Jan. 5, 1995

[30] Foreign Application Priority Data

Jun. 17, 1993 [GB] United Kingdom ................ 9312508.6

[51] Int. Cl.$^6$ ............................. C12Q 1/68; C12P 19/34; C07H 21/04
[52] U.S. Cl. ........................ 435/6; 435/91.2; 435/91.52; 435/91.51; 536/22.1; 536/24.32; 536/25.32
[58] Field of Search ............................... 435/91.2, 91.52, 435/91.51, 6; 536/22.1, 24.32, 25.32

[56] References Cited

FOREIGN PATENT DOCUMENTS

| WO92/01056 | 1/1992 | European Pat. Off. ........ C12N 15/31 |
| WO92/08805 | 5/1992 | European Pat. Off. .......... C12Q 1/68 |
| WO92/17609 | 10/1992 | European Pat. Off. .......... C12Q 1/68 |

OTHER PUBLICATIONS

S. Aabo et al., "Evaluation of a Salmonella–Specific DNA Probe by Colony Hybridization Using Non–Isotopic and Isotopic Labeling" *APMIS* 100:623–628 (1992).
S. Aabo et al., "Detection of Salmonella by Polymerase Chain Reaction" Poster Abstract, pp. 9–10 (1992).
S. Aabo et al., "Salmonella Identificationby the Polymerase Chain Reaction" *Molecular and Celluar Probes* 7:171–178 (1993).
A.R. Datta et al., "Detection of Hemolytic *Listeria Monocytogenes* by Using DNA Colony Hybridization" *Appl. and Environ. Microbiol.* 53(9):2256–2259 (1987).
R. Fitts et al., "DNA–DNA Hybridization Assay for Detection of Salmonella spp. in Foods" *Appl. and Environ. Microbiol.* 46:1146–1151 (1983).
J.M. Gopo et al., "Development of a Salmonella–Specific Biotinylated DNA Probe for Rapid Routine Identification of Salmonella" *Molecular and Cellular Probes* 2:271–279 (1988).
J.C. Guatelli et al., "Isothermal, in Vitro Amplification of Nucleic Acids by a Multienzyme Reaction Modeled after Retroviral Replication" *Proc. Natl. Acad. Sci. USA* 87:1874–1878 (1990).

U. Gyllensten, in PCR Technology. Principles and Applications for DNA Amplification, "Chapter 5, Direct Sequencing of In Vitro Amplified DNA" (Erlich, ed), pp. 45–60 (1987).
E.P. Krysinski et al., "Use of Enzyme–Labeled Antibodies to Detect Salmonella in Foods" *Appl. and Environ. Microbiol.* 33(44):947–954 (1977).
U. Landegren, "Molecular Mechanics of Nucleic Acid Sequence Amplification" *Trends in Genetics* 9(6):199–204 (1993).
A. Lund et al., "Rapid Isolation of K88 *Escherichia coli* by Using Immunomagnetic Particles"*J. Clin. Microbiol.* 26(12):2572–2575 (1988).
J.A. Mattingly, "An Enzyme Immunoassay for the Detection of All Salmonella Using a Combination of a Myeloma Protein and a Hybridoma Antibody" *J. Immun. Methods* 73: 147–156 (1984).
S.A. Minnich et al., "Enzyme Immunoassay for Detection of Salmonellae in Foods" *Appl. and Environ. Microbiol.* 43(4):877–883 (1982).
J.E. Olsen et al., "Isolation of a Salmonella–Specific DNA Hybridization Probe" *AMPIS* 99: 114–120 (1991).
J.E. Olsen et al., "DNA–Based Methods for Detection of Salmonella Enterica" Biology of Salmonella (F. Cabello et al., eds.) *NATO ASI Series* 245:373–377 (1993).
K. Rahn et al., "Amplification of an invA Gene Sequence of *Salmonella Typhimurium* by Polymerase Chain Reaction as a Specific Method of Detection of Salmonella" *Molecular and Cellular Probes* 6:271–279 (1992).
M.W. Reeves et al., "Clonal Nature of *Salmonella Typhi* and Its Genetic Relatedness to Other Salmonellae as Shown by Multilocus Enzyme Electrophoresis, and Proposal of *Salmonella Bongori* Comb. Nov." *J. Clin. Microbiol.* 27:313–320 (1989).
C.E. Rigby, "Enzyme–Linked Immunosorbent Assay for Detection of *Salmonella Lipopolysaccharide* in Poultry Specimens" *Appl. and Environ. Microbiol.* 47(6):1327–1330 (1984).
L. Rossen et al., "A Rapid Polymerase Chain Reaction (PCR)–Based Assay for the Identification of *Listeria Monocytogens* in Food Samples" *Int. J. Food Microbiol.* 14:145–152 (1991).
D.R. Scholl et al., "Clinical Application of Novel Sample Processing Technology for the Identification of Salmonellae by Using DNA Probes" *J. Clin. Microbiol.* 28(2):237–241 (1990).
H–Y Tsen et al., "Possible Use of 1.8 kb DNA Fragment for the Specific Detection of Salmonella in Foods" *J. of Fermentation and Bioengin.* 68(1):1–6 )(1989).

(List continued on next page.)

*Primary Examiner*—Kenneth R. Horlick
*Assistant Examiner*—Joyce Tung
*Attorney, Agent, or Firm*—Testa, Hurwitz & Thibeault, LLP

[57] ABSTRACT

The invention provides nucleic acid molecules for the detection and identification of Salmonella species, methods for detecting one or more Salmonella serotpes using the nucleic acid molecules of the invention as probes or primers in DNA-based detection systems and kits for carrying out the invention.

21 Claims, 6 Drawing Sheets

OTHER PUBLICATIONS

H–Y Tsen et al., "DNA Sequence of a Salmonella–Specific DNA Fragment and the Use of Oligonucleotide Probes for Salmonella Detection" *Appl. Microbiol Biotech.* 35:339–347 (1991).

M.N. Widjojoamodjo et al., "Evaluation of the Magnetic Immuno PCR Assay for Rapid Detection of Salmonella" *Eur. J. Clin. Microbiol. Infect. Dis*10(11):935–938 (1991).

S.G. Wilson et al., "Development of a Colorimetric, Second Generation Nucleic Acid Hybridization Method for Detection of Salmonella in Foods and a Comparison with Conventional Culture Procedure" *J. Food Sci.* 55(5): 1394–1398 (1990).

M.J. Wolcott, "DNA–Based Rpaid Methods for the Detection of Foodborne Pathogens" *J. Food Protection* 54(5):387–401 (1991).

Olsen et al. Isolation of a Salmonella–specific DNA hybridization probe, vol. 99, pp. 114–120, 1991.

Aabo et al. Evaluation of a Salmonella–specific DNA probe by colony hybridization using non–isotopic and isotopic labelling. vol. 100, p. 623–628.-

FIG. 1

| FIG. 1a |
| FIG. 1b |

```
  1  GATCGTGGCT GTAGCCTAAA AGAGCCCCGG CAGTATAATC ACCCCGGTCT GCAGCCGGGT
 61  GCCCATAAAG GGCATTTAAG GATGGTTGAA ATATACCTGC ATCATCATTC GCCACTGAAA
121  TAGCAAGGCT ACTGGCATTG GCCATTGTGG TCGTACTGAG TATGGCGGCA ATCATCGTTG
181  CGCAATAGCT GTATTTGTTC ACTTTTTACC CCTGAATATG AAAGTGAATA CTCTTATTTT
241  TACAAAGTAA TAAGCACAGC AGCATGATGC GCAGTGCCTA TTAAACCTTT AATATAAACT
301  AAACTCCTGC CAGCAGCGAG TCATTGAGAG GATACGTTGC CTTAATGTTG AAAAATGGTG
361  TTGAAAAACA TGCGTCAGAT ATTATTGAAT ATCCATTTTT CATTCGCTAT CTGAGTGCGA
421  GAAATTATTG GCTTCACGAT TATGCATATA ATACCATGTT TTTTGGTATC AATATGAATA
481  TCACGTGTTA TTCTTTTGAG CTCATTTTCT ATGATGGCTT CGATGTTTAT CTGTTATTAA
541  TTTTTACCGT GATAGTGTTG TCTTTAATGA TGAGAATATC TAACGGCTGT CAGGGTAATA    ST22
601  TAACCAAATT ATTGCTATCT GAATTATTAG GCAGTTATT ATTAAGGAAG AAAAAGCTGA
661  ACAAGACCAT TAATTTGCTA AAATTACTGC CCGTAGTATT ATTAAGCGCA TGTACTACAT
721  CGTATCCTCC CCAGGATACA ACATCGGCAC CCGAGTTACC CCATCGTAAC GTACTCGTTC
781  AGCAACCTGA TAACTGTAGC GTTGGCTGTC CTCAAGGAGG AAGCCAACAA ACAATCTATC
841  GCCATGTCTA TACGCTCAAT AATAATAGCG TCACGAAATT TGCCAACTGG GTTGCCTATA
901  GCGTGACAAA AACCAGCCAG GCAAGCGGTC GCCCGCGAAC TGGGCGCAGG ACCCGATTTT
961  ACCGCCCCTCG GATACGTTGG CCCTTCCGCC TATAAAAATG CCCATACGCT ATTAAAAGT
```

FIG. 1a

```
1021  CGACAGGGGG  CACCAGGCGC  CGTTGGCAGG  ATTGGGGCGG  GTATCGGACT  GGCCGTCGTT
1081  AAATTATTTA  TCGAATATTA  CGCCGCAGAA  ATCCGCCCTG  AATCAGGGAG  CATGGGCTGC
1141  ACTGGAAAAC  CGGGTGCGCG  AACTTGCCAA  ACAGGCTGAT  GTATCTGTAG  TGCACGTAGT
     ST15
1201  GACCGGCCCC  CTTTTTGAGC  GCATATCGCC  ACATTGCCAG  AAGATGCGAC  GGTAGAAATT
1261  CCCAGCGGGT  ACTGGAAGGT  TTTATTCACC  GGAATGGCGC  CGTCAAAAAG  TGAAGGAAAT
     ST14
1321  TACGCTGCAT  TTATTATGGA  TCAGAATACG  CCCCGTTCGG  CGAATTTTTG  CGACTATCAG
1381  GTTACCGTGG  AGCCTATCGA  ACATAAAGCG  AAGCCAGTGC  TGACGCTGTG  GTCTGCTTTG
1441  CCTGAAGCGG  TAGCCAGCGA  ACAAAGGGGA  GTCTGGGCCA  GAAGTTAGGT
1501  TGTCGATGAG  AAGCGCTATA  CGGCGCGTAG  GAGAAACCCT  GTCAAGGGTC
1561  TTGATTTGCT  ATAGAGTGAT  GCAATCTCCC  TTTTTTTAGT  GTTACCATCA  TCATGCCGGA
     ST11
1621  CGAAGATAGC  GATTTTCGTC  TGTGTCGAAG  GTTGTGCGCC  AATTAGCAA   TGGTTGGCTA
1681  GATGGATACA  CAACTTACTG  TCAATAAATT  CATTTTCTCT  TTGTATGTGA  TCTTGCGTAA
1741  TAAGTACAAT  CCTTCATTCA  CATCCATTCT  CGTTCGTTTA  AACCTGTTTC  ACCAGTTCCG
1801  CGTCATTACT  GGTAATAGCG  GATATATATG  TTTCATACCG  TTTTACATTG  ATCCCTTTCG
1861  CGCCGTAAGA  TGTACGTACC  TAATCTAACT  TAAGCAGGA   ACTGTCATTC  ATAACACAGA
1921  GTTTATTGGT  ATCAATGGTA  GATTATATTA  CGGTGACAAT  CTCGGGATGA  TC
```

FIG. 1b

| | |
|---|---|
| JE0402-1 | 5' 793-TTATATTACCCTGACAGCCGTTAGATATTCTCATCATTAAAGACAACACT-3' 695 |
| Sal. typhimurium[1] | ------------------------------------------------- |
| Sal. berta[2] | ---------AC--------------------------GCG--------- |
| Sal. chol.[3] | ---------AC--------------------------GCG---G----- |
| Sal. dublin[4] | ---------AC--------------------------GCG--------- |
| Sal. enteritidis[5] | ---------AC--------------------------GCG--------- |
| Sal. gallinarum[6] | ---------AC--------------------------GCG--------- |
| Sal. gallinarum[6] | ---------AC--------------------------GCG------G-- |
| Sal. pullorum[7] | ---------AC--------------------------GCG--------- |

FIG. 4

SALMONELLA IDENTIFICATION BY THE POLYMERASE CHAIN REACTION

This invention relates to the detection and identification of Salmonella species.

The incidence of salmonellosis has increased significantly during the last two decades in several western countries. In general the human population is infected by Salmonella via contaminated foods and water, but transmission occurs, to a minor extent, by direct contact with infected animals. Standard culture methods are still widely used for detection of Salmonella in foods, but control of the infection depends increasingly on the availability of rapid and precise diagnostic tests for monitoring of the primary animal production, different food processing steps and of the final food products. For this purpose several rapid methods for Salmonella detection have been developed.

These methods include enzyme immuno assays using polyvalent somatic or flagellar antibodies (Krysinski, E. P. and Heimsch, R. C. (1977) Applied and Environmental Microbiology 33, 947–954; Minnich, S. A., Hartman, P. A. and Heimsch, R. C. (1982) Applied and Environmental Microbiology 43, 877–883; Rigby, C. E. (1984) Applied and Environmental Microbiology 47, 1327–1330); monoclonal antibodies (Mattingly, J. A. (1984) Journal of Immunological Methods 73, 147–156); DNA hybridization assays using DNA polynucleotide probes (Fitts, R., Diamond, M., Hamilton, C., and Neri, M. (1983) Applied and Environmental Microbiology 46, 1146–1151); Gopo, J. M., Melis, E., Filipska, E., Meneveri, R. and Filipski, J. (1988) Molecular and Cellular Probes 2, 271–279; Tsen, H. Y., Chen, M. H., Shieh, J. S., Wang, S. J. and Hu, N. T. (1989) Journal of Fermentation and Bioengenering 68, 1–6; Scholl, D. R., Kaufmann, C., Jollick J. D., York, C. K., Goodrom, G. R., and Charache, P. (1990) Journal of clinical microbiology 28, 237–241; Olsen J. E., Aabo, S., Nielsen, E. O., and Nielsen, B. B. (1991) APMIS 99, 114–120) and oligonucleotide probes from ribosomal RNA genes (Wilson, S. G., Chan, S., Deroo, M., Vera-Garcia, M., Jonson, A., Lane, D., and Halbert, D. N. (1990) Journal of Food Science 55, 1394–1398) or from single copy target sequences (Tsen, H. Y., Wang, S. J., Roe, B. A., Green, S. S. (1991) Applied Microbiology and Biotechnology 35, 339–347).

The polymerase chain reaction (PCR) has been used to detect gene alterations in connection with sickle cell anaemia and a number of reports have been published on PCR for detection of food borne pathogens e.g. Mycobacteria, Shigella, Verotoxin producing *Escherichia coli,* Yersinia and Listeria. A method for Salmonella specific detection, combining immunomagnetic separations (Lund, A., Hellemann, A. L. & Vartdal, F. (1988) Journal of Clinical Microbiology 26, 2572–2575) and PCR on pure cultures of bacteria has recently been published (Widjojoatmodjo, M. N., Fluit, A. C., Torensma, R., Keller, B. H. I., and Verhoef, J. (1991) European Journal of Clinical Microbiology and Infectious Diseases 10, 935–938).

The above 1991 publication of J. E. Olsen et al described a Salmonella specific DNA hybridisation probe comprising a 2.3 kb fragment of the *Salmonella typhimurium* LT2 chromosome. This fragment was produced by preparing a library of *S.typhimurium* LT2 DNA containing 6800 clones by shot-gun cloning of EcoRI/Hind III fragments. The sequence of a major fragment of the above 2.3 kb fragment is shown in FIG. 1 (SEQ I.D. NO. 1). This is the product of endonuclease restriction of the 2.3 kb fragment with Sau3A employing partial digestion. Certain regions of this provide primers and probes of use in identifying Salmonella species.

The present invention is based on using certain fragments of the above genomic DNA from *Salmonella typhimurium* LT2 (or corresponding nucleic acid fragments having the same sequence of bases, including RNA, PNA (peptide nucleic acid) etc.) as primers in PCR and other amplification systems, in particular certain fragments corresponding to regions of the genome which are highly conserved in Salmonella species. This enables target nucleic acid sequences from Salmonella to be selectively amplified and thus detected. Fragments corresponding to conserved regions are useful in detecting and identifying Salmonella species generally, while fragments from less conserved regions are useful for identifying infections from serogroup B which includes *S.typhimurium* or *S.typhimurium* itself and completely unique fragments may be used for identifying *S.typhimurium* LT2. The fragments may also be used as hybridisation probes. RNA based oligonucleotides corresponding to the fragments are also of use as explained below.

Nucleic acid based methods of detection have recently proliferated and are available for detection of DNA or RNA from the target organism. A useful review is found in the article by M. J. Wolcott in J. Food Protection 54, (5), pp. 387–401, 1991, Typical techniques include solid phase capture by hybridisation probes, PCR, Q-Beta-replicase amplification and Self Sustained Sequence Replication (3SR).

According to the present invention we provide single stranded DNA of the sequence shown in FIG. 1 (SEQ I.D. NO. 1) of the drawings and the DNA sequences complementary thereto and analogues and fragments thereof hybridising selectively to the DNA or RNA of one or more Salmonella serotypes.

The term "complementary" as used above in relation to single stranded DNA includes DNA sequences with matching bases to the DNA sequence of interest and which hybridise with the stated sequence regardless of orientation.

The term "analogues" as used above in relation to single stranded DNA includes corresponding RNA sequences as well as chemically modified forms of nucleic acids and molecules with altered backbone chains such as PNA where the ribose units of the backbone are replaced by other units such as amino acids or peptides but the sequence of bases is retained and the molecule hybridises in the same way as the said DNA.

As indicated above, certain regions of the above DNA sequence are highly conserved. FIG. 2 of the drawings gives the sequence from bases 1247 to 1689 and indicates variants observed in a number of Salmonella serotypes. It will be seen that the regions termed ST11 (bases 1655 to 1679), ST14 (bases 1367 to 1390) and ST15 (bases 1251 to 1274) are completely conserved and are thus believed to be capable of hybridising to DNA from substantially all Salmonella serotypes.

The following fragments of the sequence of FIG. 1 (SEQ I.D. No. 1) have been investigated:

| Oligonucleotide | | | | Position |
|---|---|---|---|---|
| ST2 | TACTGAGTAT GGCGGCAATC ATCG | (SEQ ID NO:2) | 154–177 |
| ST3 | AGGACCCCGA TTTACCGCCC T | (SEQ ID NO:3) | 948–968 |
| ST4 | AAGTTGTGTA TCCATCTAGC CAACC | (SEQ ID NO:4) | 1672–1696 |
| ST6 | CAGCGAGGTG AAAACGACAA AGGGG | (SEQ ID NO:5) | 1455–1479 |
| ST7 | GGCGATAGAT TGTTTGTTGG CTTCCT | (SEQ ID NO:6) | 818–843 |
| ST9 | ACAGGGTTTC TCCGTTATCT TTCTACGC | (SEQ ID NO:7) | 1525–1552 |
| ST11 | AGCCAACCAT TGCTAAATTG GCGCA | (SEQ ID NO:8) | 1655–1679 |
| ST14 | TTTGCGACTA TCAGGTTACC GTGG | (SEQ ID NO:9) | 1367–1390 |
| ST15 | GGTAGAAATT CCCAGCGGGT ACTG | (SEQ ID NO:10) | 1251–1274 |
| ST17 | GCGTCAGATA TTATTGAATA TCC | (SEQ ID NO:11) | 372–394 |
| ST21 | GGGAGGATAC GATGTAGTAC ATGCGC | (SEQ ID NO:12) | 706–731 |
| ST22 | TTACCCTGAC AGCCGTTAGA TATTCTC | (SEQ ID NO:13) | 572–598 |

Three further fragments have been investigated:

ST1   TTACCCTGAC AGCCGTAGAT ATCTC  (SEQ ID NO:14) (modification of ST22)

ST5   CCGCTACTCC GCCCTAATCC ACAT   (SEQ ID NO:15) 2186 to 2009

ST8   CGGCTTCAGG CTTTCTCTTA TTGGAC (SEQ ID NO:16)  −84 to −59

ST5 and ST8 are from regions flanking the sequence of FIG. 1 (SEQ I.D. NO. 1) in the native sequence.

Hybridisation may, of course, take place under various conditions of stringency and for the greatest selectivity, conditions of high stringency are appropriate, for example a hybridisation temperature of 65° C. and buffer strength of 6xSSC. However, useful information can be derived at lower conditions of stringency, for example at hybridisation temperatures in the range 48–65° C. and/or buffer strengths in the range 1-4SSC. In testing for hybridisation, it may be preferred to perform the actual hybridisation step under low stringency conditions, eg. 45° C., followed by washing with buffer at higher stringency. The term hybridising under high stringency conditions, as used herein thus includes maintenance of hybridisation under high stringency washing conditions.

The minimum number of bases in a sequence hybridising under high stringency conditions is about 15. It will be seen that the conserved region ST11 has 36 bases, ST14 has 26 bases and ST15 has 30 bases. For use in identification of Salmonella generally by hybridisation to target Salmonella DNA or RNA, either as amplification primers or hybridisation probes, one may thus use single stranded oligonucleotides containing sequences of at least 15 consecutive bases from ST11, ST14 or ST5. For most reliable hybridisation, sequences of at least 20 of said bases are preferred. It will be appreciated that such conserved sequences may have other DNA attached which may be less conserved or even completely non-hybridising. For use in the DIANA detection system, as discussed hereinafter, the hybridising sequence may advantageously carry non-hybridising DNA sequences capable of binding to solid supports eg. via DNA binding proteins or specific binding partners such as biotin/streptavidin.

For use in hybridisation to DNA or RNA from the general sero group which includes *S.typhimurium*, it is possible to use oligonucleotide fragments according to the invention which contain sequences only conserved within that group. These include the sequences ST22 referred to above.

For use in detection of *S.typhimurium* specifically, it is possible to use oligonucleotide fragments according to the invention which are specific to *S.typhimurium* strains.

Fragments of the oligonucleotide sequence according to the invention specific to *S.typhimurium* LT2 can be used for detection of this particular strain.

It will be appreciated that in most instances the target DNA to be detected will be double stranded and that hybridisation to either of the strands can be used for identification. Thus, for use as hybridisation probes, both the specified oligonucleotide fragment as derived from FIG. 1 (SEQ I.D. NO. 1) and its complement are usable.

However, methods of detection based on amplification present a more powerful and sensitive tool for identification and in this case the oligonucleotide functions as a primer. Since the primer only functions to initiate chain extension from its 38-terminus, it is required to hybridise to the 3' end of one of the strands of the target DNA sequence to be amplified; where the oligonucleotide is a fragment of the coding strand of the Salmonella DNA it will hybridise to the complementary strand of the target Salmonella DNA and vice versa.

Thus a further aspect of the invention provides a method of detecting one or more Salmonella serotypes wherein at least one nucleic acid molecule according to the invention is used as a probe or primer in a DNA-based detection system.

The principal amplification technique to be used in accordance with the invention is PCR. In this case, in classical PCR, two primers are required, hybridising to opposing strands of the target DNA. It is possible to select pairs of oligonucleotides according to the invention to meet this requirement. Thus, for example, the oligonucleotides ST14 and ST15 are derived from the coding strand of *S.typhimurium* DNA and hybridise to the complementary strand of the target DNA while ST11 hybridises to the coding strand.

Thus, typical PCR primer pairs can comprise ST14/ST11 or ST15/ST11. The latter combination has proved particularly effective.

It is also possible, however, to carry out PCR detection using a single specific primer by ligating a standard sequence or tail to the target DNA, to provide an hybridisation site for a standard PCR primer. This may be achieved by restriction of the target ds DNA at a known site and ligating the standard sequence to the sticky end so produced. This means that, provided conveniently placed restriction sites exist on either side of a conserved sequence, the target ds DNA may be cleaved at one of such sites and ligated to a standard sequence; this may be followed by strand separation to provide either the coding strand or the complementary strand in a form which may be amplified by PCR using the appropriate oligonucleotide from either orientation of the conserved sequence, each serving to initiate chain extension from its 3' end towards the sequence ligated at the site of restriction. One such PCR system is the so-called Vectorette system where a designed oligonucleotide having a short sequence mismatched with the target DNA is ligated at a chosen restriction site. After a single chain extension of the chosen specific primer past the ligated sequence, a primer corresponding to the mismatched sequence can be used to initiate extension in the opposite direction and can serve as a PCR primer in subsequent cycles.

It will thus be appreciated that the preferred sequences ST11, ST14 and ST15 or fragments thereof may have the sequences shown in FIG. 2 (SEQ ID NOS: 20–22) or may be complementary thereto. In fact, the oligonucleotide ST11 which directs extension in the opposite sense to ST14 and ST15 is in the form complementary to that shown in FIG. 2.

In the Self-Sustained Sequence Replication (3SR) process, probe/primers are used which carry polymerase binding sites permitting the action of reverse transcriptase to amplify target RNA or ss DNA. For use in this process, DNA oligonucleotides according to the invention thus carry a polymerase binding sequence at the 3'-terminus. Thus the DNA sequence for the T7-RNA polymerase promotor may be linked to a sequence for transcription initiation attached to one or both the target specific primers- An example of such sequences is

```
AATTTAATAC GACTCACTAT AGGGATC(SEQ ID NO:17) or

AATTTAATAC GACTCACTAT AGGGA (SEQ ID NO:18)
                                       transcription initiation
      T7 promotor
```

(Guatelli et al., 1990, Proc. Natl. Acad. Sci. USA, 87, 1874–1878.)

In the Q-beta replicase amplification system, an immobilised probe captures one strand of target DNA and is then caused to hybridise with an RNA probe which carries as template region, a tertiary structure known as MDV-1 for an RNA-directed RNA polymerase, normally Q-beta replicase. The capture probe may be DNA or RNA and thus, for this function, an immobilised DNA or RNA oligonucleotide fragment according to the invention may be used. In addition, an RNA oligonucleotide according to the invention may carry the MDV-1 structure at the 3'-end.

The Ligase Amplification Reaction (LAR) hybridises two oligonucleotide probes to adjacent positions on the target nucleic acid so that ligation, eg. using T4 ligase, produces a longer sequence which, after strand separation, can function as a template for further hybridisations and ligations. It is thus possible to use as LAR probes, two adjacent oligo- nucleotide sequences from one of the conserved sequences, eg. ST11, ST14 or ST-15 (to provide general Salmonella detection) or other oligonucleotides according to the invention to provide more specific Salmonella detection, e.g. S. typhimurium.

In the DIANA diagnostic system, PCR is effected using nested primers, that is a first pair of primers to amplify the target nucleic acid in a first series of cycles, and a second pair of primers hybridising between the first primer pair in a second series of cycles. The inner primers used in the second cycle carry, respectively, means for immobilisation to permit capture of the amplified DNA and a label or means for attachment of a label to permit recognition. The means for immobilisation may, for example, be a hapten such as biotin or digoxigenin while the means for attachment of a signal may include a different hapten or, in a preferred embodiment, a 5'-non-hybridising DNA sequence which is capable of binding to a DNA-binding protein carrying an appropriate label. The immobilisation means may also be attached via a 5'-non-hybridising DNA sequence. Thus, for this procedure, oligonucleotides according to the invention may carry 5'-non-hybridising DNA sequences which carry means for immobilisation or are attached to a solid support and/or carry a label capable of attachment to a label, eg. an enzyme, a fluorescent substance or a radionuclide.

Solid supports for immobilisation include microtitre wells, dipsticks, fibres and particles carrying a binding partner for the means for immobilisation, eg. streptavidin (for biotin) or an anti-hapten antibody (for other haptens). Magnetic particles are particularly advantageous, for example the superparamagnetic, monodisperse particles sold by Dynal A/S, Oslo, Norway.

Hybridisation probes based on oligonucleotides according to the invention may usefully either capture the target nucleic acid or label it with a signal. Such probes will thus be essentially the same as one of the second pair of primers described above for the DIANA system.

The oligonucleotides according to the invention may be synthesised by known techniques using conventional machine synthesizers such as the Cyclone DNA synthesizer (Biosearch Inc.).

The invention also extends to kits for detection of Salmonella comprising at least one oligonucleotide according to the invention. Such kits will normally also contain such additional components as:

(a) for PCR, a polymerase and at least one other oligonucleotide primer according to the invention; the oligonucleotides both being DNA based and hybridising to opposite strands of the target DNA;

(b) for DIANA, a polymerase and PCR oligonucleotide primers according to the invention provided with means for immobilisation and means for labelling;

(c) for 3SR, a reverse transcriptase and a further DNA oligonucleotide primer according to the invention, both oligonucleotides being provided with a polymerase binding site;

(d) for LAR, a ligase and a further oligonucleotide primer according to the invention adjacent to the first in the sequence of FIG. 1 (SEQ I.D. No. 1);

(e) for Q-beta replicase amplification, an RNA directed RNA polymerase and an RNA probe with a 5'-MDV-1 structure or fragment thereof, the capture oligonucleotide being immobilised or permitting immobilisation.

In all the above kits, nucleotide bases will normally be supplied together with appropriate buffers.

BRIEF DESCRIPTION OF THE DRAWINGS

FIG. 1 shows the sequence of single strand DNA used in the present invention. The above 1991 publication of J. E. Olsen et al. described a Salmonella specific DNA hybridization probe comprising a 2.3 kb fragment isolated from the *Salmonella typhimunium* LT2 chromosome. The sequence of a major fragment of the 2.3 kb fragment is shown in FIG. 1. This is the product of endonuclease restriction of the 2.3 kb fragment with Sau 3A employing partial digestion.

FIG. 4 shows the sequence alignment of strains of Salmonella in the region of the *Sal. typhimurium* specific oligonucleotide probe, ST22 used in Example 2. The sequence of the DNA-fragment JE0402-1, SEQ ID NO:22 which originates from *Sal. typhimurium* is shown as reference. Bases that are specific for *Sal. typhimurium* have been underlined. Only bases that deviate from the JE0402-1 sequence are indicated in other strains. A: adenine, C: cytosine, G: guanine, T: thymine. Number of strains tested: 1: three with the same sequence; 2: two with the same sequence; 3: one; 4: three with the same sequence; 5: three with the same sequence; 6: two strains with one base difference; 7: two strains with the same sequence.

Figure 2A:
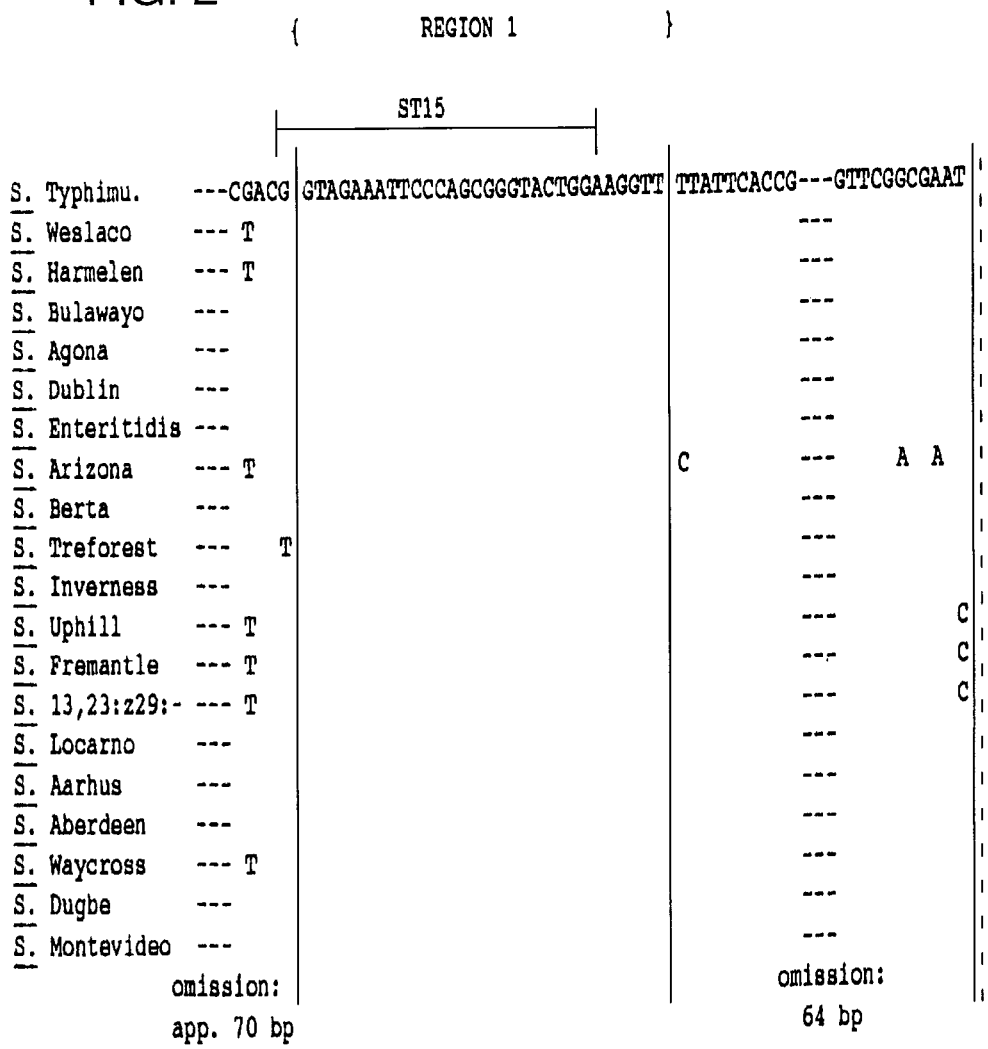
FIG. 2 shows the alignment of nucleotide sequences from bases 1247 to 1689 and indicates variants observed in a number of Salmonella serotypes.

The following Examples are given by way of illustration only.

EXAMPLE 1

Use of oligonucleotide probes/primers in hybridisation dot-blot and PCR assays for the detection of Salmonella Strains and media:

146 Salmonella strains (Table 2) and 86 non-*Salmonella Enterobacteriaceae* strains (Table 3) were used in this study. Cells were grown in Lura Bertani broth (25) at 37° C. The *S Typhimurium* LT2 strain from which the probe fragment had been cloned was used as positive control, and *E. coli* strains JM103 and HB101 served as negative controls in PCR.

Oliaonucleotide synthesis, labelling and hybridisation

Oligonucleotides were synthesized on a Cyclone DNA Synthesizer (Biosearch Inc. Millipore, Tåstrup, Denmark) according to the manufacturers instructions and were 3'-end labelled with gamma $^{32}$P-DATP (Amersham, Aylesbury, England) according to Maniatis et al. (25) using terminal transferase (Boehringer Mannheim, Kvistgaard, Denmark). The sensitivity and specificity of the primers were tested by hybridisation of labelled oligonucleotides at 50° C. in 6xSSC (1xSSC=0.15M NaCl, 0.015 Na-Citrate, pH 7.0) to dot-blots containing approximately $10^8$ bacterial cells, lysed as described by Datta et al. (Datta, A. R., Wentz, B. A. and Hill, W. E. (1987). Detection of Hemolytic *Listeria monocytoaenes* by using DNA colony hybridisation. Applied and Environmental Microbiology 53, 2256–2259.) Post hybridisation washes were performed in 6xSSC at temperatures of 55° C., 59° C., 61° C. and 65° C. Autoradiograms were developed between each wash according to the instructions of the supplier (Amersham).

DNA-sequencing

The sequence of the 2.3 kb Salmonella specific DNA fragment shown in FIG. 1 (SEQ I.D. NO. 1) formed the basis for primer selection. Sequencing of corresponding regions in 19 different serovars was done following asymmetric PCR carried out as described by Gyllensten (Gyllensten, U. (1989)). Direct sequencing of in vitro amplified DNA. In PCR Technology. Principles and applications for DNA amplification. (Erlich, H. A. ed.) pp 45–60. New York, Stockton Press.) using the primers ST3 and ST4 as PCR primers and ST6 and ST9 as sequencing primers (FIG. 1 SEQ I.D. NO. 1).

PCR assay

Crude extraction of DNA from pure cultures of Salmonella was done by alkaline lysis at 94° C. according to Rossen et al. (Rossen, L., Holmstrom, K., Olsen, J. E., and Rasmussen, O. F. (1991). A rapid polymerase chain reaction (PCR)-based assay for the identification of *Listeria monocytoaenes* in food samples. International Journal of Food Microbiology 14, 145–152.). Five µl of the solution was transferred to a tube containing 100 µl of a mixture of 50 mM KCl, 2.5 mM MgCl$_2$, 10 mM Tris, HCl pH 8.3, 200 µM of each of the dNTP's (Boehringer Mannheim) 1 µM of each primer, 0.02% gelatine (Difco, Detroit, USA) 0.5% Tween 20 and 2.5 units Taq-polymerase (Promega, Madison, USA). The PCR reaction mixture was overlayed with 100 µl paraffin oil. A 30 cycle PCR was carried out using the following conditions: denaturation at 94° C. for 1 minute, annealing at 57° C. for 1 minute and elongation at 72° C. for 2 minutes. The elongation step in the last cycle was 10 minutes. PCR products were visualized by agarose gel electrophoresis using standard methods.

RESULTS

Figure 2B:
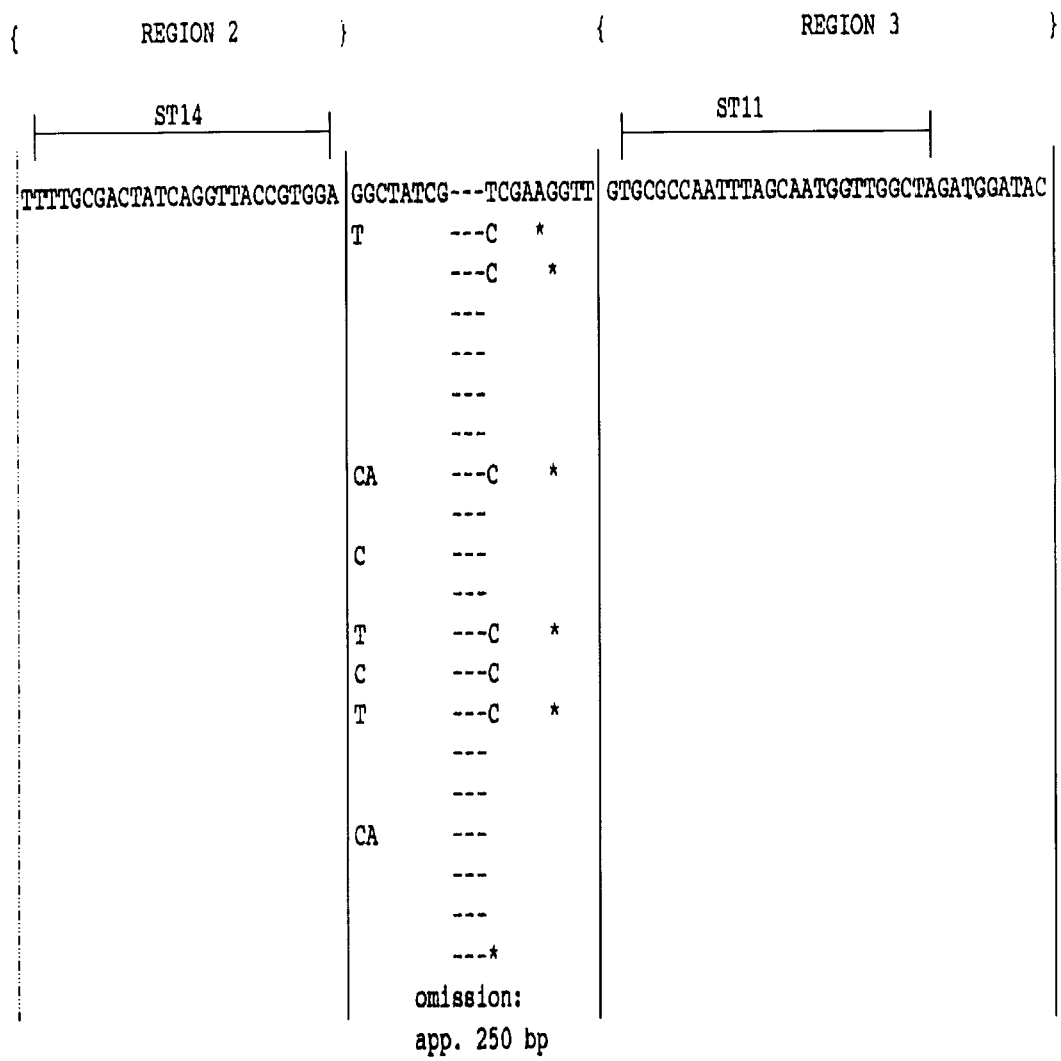

Eight oligonucleotide sequences (ST1–ST8) (FIG. 1 SEQ I.D. NO. 1) were selected from the sequence and tested for their ability to discriminate between Salmonella and non-Salmonella bacteria by hybridisations to dot blots with pure cultures of 15 Salmonella and 15 non-Salmonella strains. The hybridisations were carried out at low stringency. High stringency conditions were obtained by four successive washings at increasing temperatures. As seen from Table 1, the primers ST3, ST4, ST5 and ST7 gave no false positive reactions while one to four false negative results were obtained with these oligonucleotides at the high stringency washing temperature of 65° C. This indicated some interserovar sequence heterogeneity of the 2.3 kb fragment. In order to localize conserved sequences, two regions of the fragment were sequenced in 19 different Salmonella serovars belonging to subspecies I–IV. The serovars are listed in FIG. 2. The position of the two regions, app. 220 bp and 160 bp in size, are shown in FIG. 1 (SEQ I.D. NO. 1). The 19 serovars showed a mean of 16.5 base differences (4.2%) but, as seen from FIG. 2, all serovars shared three conserved subregions of 26, 30 and 36 basepairs, respectively. From each subregion, one oligonucleotide was selected as a putative PCR primer. The primers ST14 and ST15, both 24 bases, were selected with opposite orientation in relation to ST11 (25 bases) (FIG. 2).

The oligonucleotides ST11, ST14 and ST15 were evaluated by hybridisation as described above to 75 Salmonella strains and 45 non-Salmonella strains belonging to Enterobacteriaceae. ST11 and ST15 each gave 3 false negative reactions at all stringency levels whereas ST14 showed 5 false positive at the lowest stringency temperature and 6 false negative reactions at all stringency temperatures. The strains that showed false reactions in the dot-blot hybridisation assays, were tested in a PCR assay. Of the six Salmonella strains giving false negative hybridisation results for either ST11, ST14 or ST15, the PCR primer set ST11/ST15 gave only one false negative PCR reaction i.e. *S. arizona* subspecies IIIa. PCR testing of the primer set ST11/ST14 revealed two false negative reactions i.e. *S. arizonae* IIIa and S. Blockley. No false positive reactions were noted with the two primer sets.

The primer set ST11/ST15 gave a PCR product of 429 basepairs. These primers were evaluated for their ability to identify Salmonella in pure cultures of bacteria. As seen from Table 2, 144 of 146 Salmonella strains (116 of 118 serovars) were correctly identified, while two strains belonging to subspecies IIIa werefalse negative. No PCR-products were produced from the 86 non-Salmonella strains listed in Table 3.

TABLE 1

Hybridization of 8 potential PCR primer oligonucleotides to 15 Salmonella and 15 non-Salmonella strains at varying stringency.

| Washing temp. | Primer* | | | | | | | |
|---|---|---|---|---|---|---|---|---|
|  | ST8 | ST2 | ST1 | ST7 | ST3 | ST6 | ST4 | ST5 |
| Non-Salmonella | No. of false positives | | | | | | | |
| 55° C. | 0 | 4 | 0 | 0 | 0 | 0 | 0 | 1 |
| 59° C. | 0 | 0 | 0 | 0 | 0 | 0 | 0 | 1 |
| 61° C. | 0 | 0 | 0 | 0 | 0 | 0 | 0 | 0 |
| 65° C. | 0 | 0 | 0 | 0 | 0 | 0 | 0 | 0 |
| Salmonella | No. of false negatives | | | | | | | |
| 55° C. | 4 | 2 | 14 | 4 | 4 | 1 | 0 | 0 |
| 59° C. | 4 | 8 | 14 | 4 | 4 | 1 | 0 | 0 |
| 61° C. | 4 | 9 | 14 | 4 | 4 | 1 | 2 | 7 |
| 65° C. | 5 | 12 | 14 | 4 | 4 | 1 | 4 | 7 |

*The oligonucleotides are listed in the order they are positioned on fragment JEO402-1 (see FIG. 1)

TABLE 2

Evaluation of a Salmonella specific PCR-assay using ST11/ST15 by testing pure cultures of Salmonella bacteria.

| Subspecies | No. tested | | No. of positive | |
|---|---|---|---|---|
|  | Strains* | Serovars | Strains | Serovars |
| S. enterica | 95 | 69 | 95 | 69 |
| S. salamae | 23 | 21 | 23 | 21 |
| S. arizonae | 18 | 18 | 16 | 16 |
| S. houtenae | 8 | 8 | 8 | 8 |
| S. bongori | 1 | 1 | 1 | 1 |
| S. indica | 1 | 1 | 1 | 1 |
| Total: | 146 | 118 | 144 | 116 |

*Strains were obtained from Statens Seruminstitut, Copenhagen, Denmark and Department of Veterinary Microbiology, The Royal Veterinary and Agricultural University of Copenhagen, Denmark.

TABLE 3

86 Enterobacteriaceae strains, all tested negative with Salmonella PCR primers ST11/ST15.

| Genus | Species | No. of strains* |
|---|---|---|
| Cedecea | davisae | 1 |
| Cedecea | lapagei | 1 |
| Cedecea | neteri | 1 |
| Citrobacter | amaionaticus | 1 |
| Citrobacter | freundii | 3 |
| Citrobacter | diversus | 2 |
| Edwardsielia | hoshinae | 1 |
| Edwardsiella | tarda | 2 |
| Enterbacter | aerogenes | 1 |
| Enterbacter | agglomerans | 1 |
| Enterbacter | amnigenus | 1 |
| Enterbacter | asburiae | 1 |
| Enterbacter | gergoviae | 1 |
| Enterbacter | rubidea | 1 |
| Enterbacter | sakazakii | 1 |
| Enterbacter | taylorae | 1 |
| Erwinia | herbicula | 2 |
| Escherichia | coli | 21 |
| Ewingella | americana | 1 |
| Hafnia | aivii | 1 |
| Klebsiella | oxytoca | 1 |
| Klebsiella | pneumoniae | 1 |
| Koserella | trabulsii | 1 |
| Leminorella | grimontii | 2 |
| Lerninorella | richardii | 2 |
| Moellerella | wisconsensis | 3 |
| Morganella | morganii | 1 |
| Obesumbacterium | biogroup 1 | 1 |
| Obesumbacterium | biogroup 2 | 1 |
| Proteus | mirabilis | 6 |
| Providentia | heimbachae | 1 |
| Providentia | stuartii | 3 |
| Rhanella | aquatilis | 1 |
| Serratia | marcescens | 2 |
| Serratia | oderiferi | 1 |
| Shigella | flexneri | 1 |
| Shigella | sonnei | 2 |
| Tatumella | ptyseos | 1 |
| Xenorhabdus | luminescens | 1 |
| Yersinia | enterocolitica | 5 |
| Yersinia | pseudotuberculosis | 4 |

*All strains originate from the strain collection of The Department of Veterinary Microbioiogy, The Royal Veterinary & Agricultural University, Copenhagen, Denmark.

EXAMPLE 2

Use of oligonucleotide probes in colony hybridisation assays for the detection of Salmonella Bacterial strains used in the study comprised 141 strains of Salmonella and 28 strains of 19 other genera of Enterobacteriaceae. Details on the number of Salmonella serotypes, the distribution according to Salmonella subspecies, and species of Enterobacteriaceae can be seen from the results section (Tables 4 and 5).

Figure 3:
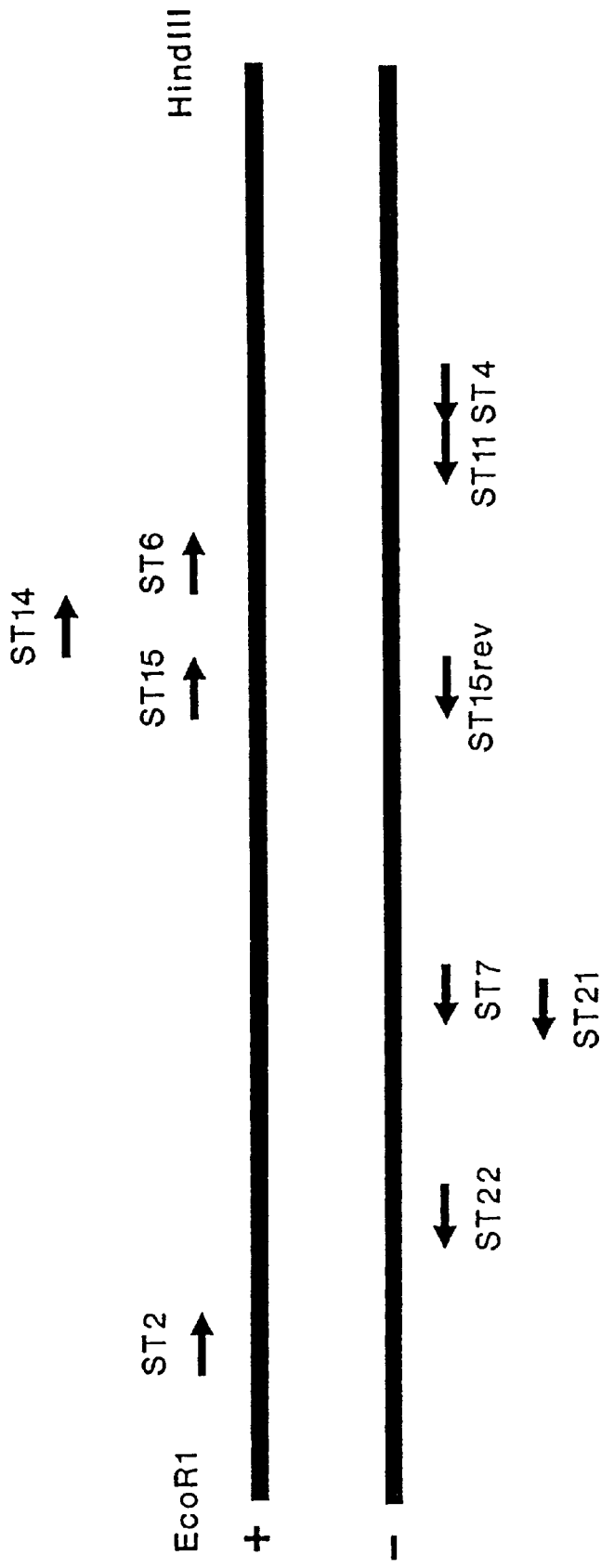
FIG. 3 shows the position of oligonucleotides used as probes or in sequencing reactions in Example 2 on the DNA-fragment JE0402-1 (Olsen et al., (1991), supra). Numbering is according to Aabo et al., 1993 (Aabo, S., Rossen, L., Rasmussen, O. F., Sorensen, P. D., and Olsen, J. E. (1993), Molecular and Cellular Probes 7, 171–178).

Oligonucleotide probe-sequences can be seen from Table 6. The location of the oligonucleotides on the DNA-fragment, JE0402-1 (Olsen et al. 1991, supra) is indicated in FIG. 3. Oligonucleotides were purchased from DNA-technology (Aarhus, Denmark). For use as hybridization probes, the oligonucleotides were 3'-end labelled with Dig-11-dUTP (Boehringer, Mannheim) as described by Thomas et al. (1991) (Thomas, A., Smith, H. R., Willshaw, G. A. & Rowe, B. (1991) Molecular and Cellular Probes 5, 129–135.).

Colony hybridization with Dig-11-dUTP labelled probes was performed as described by Thomas et al. (1991, supra).

The hybridization temperature used with each oligonucleotide can be seen from Table 6. Post hybridization was performed for 2×10 minutes at room temperature and 1×5 minutes at the hybridization temperature, as described by Aabo et al. (1992) (Aabo, S., Thomas, A., Hall, M. L. M., Smith, H. R. and Olsen, J. E. (1992). APMIS 100, 623–628.).

DNA-sequencing was performed using the Sequenase 2.0 sequencing kit (USB, Amersham, Copenhagen) on single stranded DNA isolated from double stranded PCR-products using para-magnetic beads (M280, Streptavidin coated, Dynal, Oslo) and the PCR and immunomagnetic capture protocol recommended by the supplier of the beads. The oligonucleotides used to prime the amplification and the sequencing primer are shown in Table 6.

RESULTS

Genus specific oligonucleotides

Five oligonucleotides were synthesized and analyzed for their ability to detect strains of Salmonella without cross hybridization to non-Salmonella bacteria. Initially 19 strains of bacteria were hybridized to the oligonucleotide probes, and as seen from Table 7, the probe, ST4, detected all strains of Salmonella, while the remaining oligonucleotide probes missed one of three strains each; however, none of the oligonucleotides reacted with the three strains of *Escherichia coli* included.

Two of the oligonucleotide probes ST4 and ST15 were selected for further analysis. However, for both oligonucleotides to hybridize to the same DNA strand, which is required for "sandwich hybridization assays" (see Wolcott, M. J. (1992) Clinical Microbiology Reviews 5, 370–386 for details on this assay format), the complementary sequence to oligonucleotide ST15, ST15rev, was used in this hybridization to a large collection of Salmonella and non-Salmonella bacteria (Table 4). For the same reason, the hybridization temperature was chosen to be 55° C. for both oligonucleotide probes. The strains analyzed in Table 7 were included in this analysis again.

The oligonucleotide ST4 detected all the 93 strains of Salmonella analyzed and ST15rev detected all but one. The strain missed by ST15rev belonged to Salmonella subspecies V and was the same strain as missed by ST15 in the initial screening (Table 7). No signals were seen from the 28 non-Salmonella strains tested, except for one strain of *Edwardsiella tarda* with probe ST4.

Sal. typhimurium specific oligonucleotide

In a search for PCR-primers, Aabo et al. (1993, supra) noted that an oligonucleotide, ST1, deduced from the same DNA fragment as analyzed in this paper, only detected *Sal. typhimurium* among 15 strains of Salmonella analyzed. The DNA sequence of a 114 base-pair region around ST1 was analyzed in 16 strains of 7 serotypes of Salmonella. Based on the result of this alignment (FIG. 4), an oligonucleotide probe, ST22, was synthesized and analyzed for its ability to detect strains of *Sal. typhimurium*. As seen from Table 5, the probe was specific for the 47 strains of this serotype analyzed among the 94 strains of other Salmonella serotypes and 26 non-Salmonella strains analyzed.

SUMMARY

An oligonucleotide, ST15rev, that is specific for the genus Salmonella identifies all serotypes analyzed except a member of Sal. subgenus bongori.

Only 17 serotypes belong to *Sal. bongori* and it has recently been suggested to be distinct from Salmonella as a species based on cluster analysis of isoenzyme-profiles (Reeves, M. W., Evins, G. M., Heiba, A. A., Plikaytis, B. D. and Farmer III, J. J. (1989) Journal of Clinical Microbiology 27, 313–320). Mainly due to the low prevalence, the failure to detect members of this subgenus may not be ruinous to the use of this particular probe in Salmonella detection.

An oligonucleotide provide, ST4, that detected all members of Salmonella analyzed, but which cross hybridized to one strain of *Edw. tarda* was also identified. Due to the cross hybridization it is less useful as a genus specific probe. Fortuitously, the location on the DNA-fragment JE0402-1 is such that a sandwich hybridization assay can be constructed with probe-ST15rev as a capture probe and probe-ST4 as a labelled reporter probe hybridizing to all strains that have been captured by probe ST15rev. The cross hybridization to *Edw. tarda* will not be critical in this assay format, as DNA from this bacteria will not be captured by ST15rev.

An oligonucleotide probe, ST22, was found to be specific for *Sal. typhimurium*, which differed in five base-positions from five other serotypes sequenced.

It may be assumed, that oligonucleotide probes that are specific for other important Salmonella serotypes may be identified by the same approach used to analyze other DNA-fragments, and serotyping by use of oligonucleotides can then be performed; at least for the most commonly isolated serotypes.

TABLE 4

Hybridization of digoxigenin-labelled oligo-
nucleotides ST4 and ST15rev to Salmonella and non-Salmonella strains

| Bacterium/ bacterial group | No. of strains tested | number of positive hybridizations | |
|---|---|---|---|
| | | ST4 | ST15rev |
| Salmonella[1] | 93 | 93 | 92[2] |
| Enterobacter- iaceae[3] | 28 | 1[4] | 0 |

[1]Number of strains: 73 of 62 serotypes of subspecies I (*S.* subsp. *enterica*), six of six serotypes of subspecies II (*S.* subsp. *salamae*), six of five serotypes of subspecies III (*S.* subsp. *arizonae/S.* subsp. *diarizonae*), six of six serotypes of subspecies IV (*S.* subsp. *houtenae*), one of subspecies v (*S.* subsp. *bongori*), and one of subspecies VI (*S.* subsp. *indica*).
[2]One strain of serotype V 66:Z$_{41}$:- (Brookfield) was negative.
[3]Number of strains: one *Cedecae davisae*, one *Ced. lapaqei*, one *Ced. neteri*, one *Citrobacter freundii*, one *Enterobacter sakazyki*, one *Edwardsiella hoshmare*, one *Edw. tarda*, 9 *Escherichia coli*, one *Ewingella americana*, one *Klebsiella oxytoca*, one *Kosserella tabusii*, one Klyverae sp., one *Leminorella grimontii*, one *Proteus mirabilis*, one *Providencia heimbachae*, one *Prov. stuartii*, one *Serratia oderter*, one *Ser. rubideae*, one *Shigella sonnei*, one *Yersinia enterocolitica*.
[4]One strain of *Edw. tarda* was false positive.

TABLE 5

Detection of *Salmonella typhimurium* by colony
hybridization with digoxigenin-labeile.d oligonucleotide, ST22.

| Bacteria/ bacterial group | No. of strains tested | No. of reactions: | |
|---|---|---|---|
| | | positive | negative |
| Salm. typhimurium | 47 | 47 | 0 |
| Salmonella other | 94 | 0 | 94 |

TABLE 5-continued

Detection of *Salmonella typhimurium* by colony
hybridization with digoxigenin-labeile.d oligonucleotide, ST22.

| Bacteria/ bacterial group | No. of strains tested | No. of reactions: positive | negative |
|---|---|---|---|
| serotypes[1] non-Salmonella[2] | 26 | 0 | 0 |

[1]Seventy eight serotypes: 59 of subspecies I (*Sal.* subsp. *enterica*), six of subspecies II (*Sal.* subsp. *salamae*), five of subspecies III (*Sal.* subsp. *arizonae/Sal.* subsp. *diarizonae*), six of subspecies IV (*Sal.* subsp. *houtenae*), one of subspecies V (*Sal.* subsp. *bongori*), and one of subspecies VI (*Sal.* subsp. *indica*).
[2]Number of species tested was 19 and number of genera represented was 13.

TABLE 6

Oligonucleotides used in Example 2

| Oligonucleotide | sequence 5'------ 3 | | hybridization temp. (° C.) |
|---|---|---|---|
| ST4 | AAGTTGTGTATCCATCTAGCCAACC | (SEQ ID NO:4) | 55 |
| ST6 | CAGCGAGGTGAAAACGACAAAGGGG | (SEQ ID NO:5) | 55 |
| ST11 | AGCCAACCATTGCTAAATTGGCGCA | (SEQ ID NO:8) | 55 |
| ST14 | TTTGCGACTATCAGGTTACCGTGG | (SEQ ID NO:9) | 55 |
| ST15 | GTAGAAATTCCCAGCGGGTACTG | (SEQ ID NO:10) | 50 |
| ST15rev | CAGTACCCGCTGGGAATTTCTAC | (SEQ ID NO:19) | 55 |
| ST2 | TACTGAGTATGGCGGCAATCATCG | (SEQ ID NO:2) | used for PCR |
| ST7 | GGCGATAGATTGTTTGTTGGCTTCCT | (SEQ ID NO:6) | used for PCR |
| ST21 | GGGAGGATACGATGTAGTACATGCGC | (SEQ ID NO:12) | sequencing primer |
| ST22 | TTACCCTGACAGCCGTTAGATATTCTC | (SEQ ID NO:13) | 63 |

A: Adenine, C: Cytosine, G: Guanine, T: Thymine

TABLE 7

Hybridization of digoxigenin-labelled oligonucleotides to strains of Salmonella and non-Salmonella

| Bacteria/ bacterial group | No. of strains | No of positive hybridization results | | | | |
|---|---|---|---|---|---|---|
| | | ST4 | ST6 | ST11 | ST14 | ST15 |
| Salmonella[1] | 19 | 19 | 18 | 16 | 18 | 18 |
| *E. coli* | 3 | 0 | 0 | 0 | 0 | 0 |

[1]Twelve strains of subspecies I (*S.* subsp. *enterica*), one strain of subspecies II (*S.* subsp. *salamae*), four strains of subspecies III (*S.* subsp. *arizonae/S.* subsp. *diarizonae*), one strain of subspecies IV (*S.* subsp. *houtenae*), one strain of subspecies V (*S.* subsp. *bongori*).

EXAMPLE 3

Detection of Salmonella in minced meat using PCR in comparison to standard culture techniques.

Forty eight samples of minced beef and 48 samples of minced pork were pre-enriched at 37° C. overnight in phosphate buffered peptone (Anon, Nordic Method Committee on Food, No. 71, 4 ed., 1991). The pre-enrichment cultures were used both for the PCR assay and for the standard culture method which were performed in parallel. For the culture method one ml of pre-enrichment culture was transferred to 9 ml tetrathionate broth (Anon, Nordic Method Committee on Food, No. 71, 3 ed., 1985) and 0.1 ml pre-enrichment broth was transferred to 9.9 ml Rappaport-Vassiliadis medium (RV) (Oxoid CM669). Both cultures were incubated for 20–22 hours at 41.5° C. A loop full of each culture was streaked onto BGA (CM395) and NEGL agar (Poisson 1992) and incubated for 22–24 hours at 37° C. Salmonella suspect colonies were biochemically characterised according to standard protocols (Anon. 1991, supra). For the PCR assay, one ml of pre-enrichment culture was transferred to 9 ml tetrathionate broth (Anon. 1985, supra) and 0.1 ml was transferred to 9.9 ml of RV (Merck 7700) and cultured for 7 hours at 41.5° C. Thereafter a post selective step was performed in order to eliminate Taq-polymerase inhibition by the selective medias. One ml of tetrathionate culture and 0.05 ml RV were transferred to 9 ml and 9.95 ml of Luria-Bertani (LB) broth respectively, and incubated for 14–16 hours at 37° C. Cells in five $\mu$l of LB culture were lysed in lysis buffer (0.05M NaOH, 0.25 %SDS) at 94° C. for 15 minutes and five 5 $\mu$l of the lysate were added to the PCR tube containing 100 $\mu$l of 50 mM KCl, 10 mM Tris, pH 8.3, 2.5 mM $MgCl_2$, 200 $\mu$M of each dNTP, 1 $\mu$M of each primer, ST11 5'AGCCAACCATTGCTAAATTGGCGCA3' and ST15 5GTAGAAATTCCCAGCGGGTACTG3', 0.5% Tween 20, and 0.02° C. gelatine and 2.5 units Taq-polymerase (Promega). The vial was overlayed with 100 $\mu$l paraffin oil. PCR cycling conditions were 94° C. for 1 minute, 57° C. for 1 minute and 72° C. for 2 minutes for 30 cycles. In the last cycle, the elongation step was prolonged to 10 minutes. Detection was performed by agarose gel electrophoresis in a 1.5% agarose gel followed by ethidium bromide (2 mg/l) staining, destaining in water and photographing under 254 UV light with a Polaroid Land Camera. PCR products were verified by southern blot hybridization using the 2.3 kb fragment (Olsen et al., 1991, supra), from which the primers were deduced, as probe. The probe was labelled with digoxigenin (Boehringer) as described by Aabo et al. (1992, supra). Samples were considered positive in either PCR or culture when at least one of the two selective media used gave rise to a positive result.

Of the 7 PCR positive pork samples, only 4 were positive by culture and of the 41 PCR negative pork samples 1 was positive by culture. Of the 5 PCR positive beef samples, one was positive by culture while all 43 PCR negative beef samples also came out culture negative. A fusion of the results of both meat types are summarized in Table 8. A total of 7 of the PCR results were characterised as false positive when compared to the results of the culture method. When repeated culturing from the LB cultures was performed either directly on BGA/NBGL agar or after RV (Merck 7700) culturing Salmonella was isolated from 6 of the 7 LB cultures. Based on this, the sensitivity of the PCR method was estimated to 92% and the specificity to 99% when calculations were based on the pooled results of the 96 pork and beef samples. When PCR was performed directly on pre-enrichment cultures only one of the 12 Salmonella positive samples was detected. The sensitivity of the standard culture method was estimated to 50% based on the 12 samples from which the presence of Salmonella was verified and the specificity was estimated to 100% based on the 84 negative samples.

The Salmonella specific PCR assay used in this study was found to be more sensitive that the standard culture method for identification of Salmonella in pre-enriched cultures. The sensitivity of the standard culture method was found to be as low as 50%.

TABLE 8

Comparison of standard culture technique and PCR method for detection of Salmonella in 48 samples of pork and beef meat

|  |  | Culture technique | | |
|---|---|---|---|---|
|  |  | + | − | Total |
| PCR result | + | 5 | 7[#] | 12 |
|  | − | 1 | 83 | 84 |
|  | Total | 6 | 90 | 96 |

[#]By repeated culturing from LB postenrichment broths, Salmonella was isolated in 6 of the samples. Based on this, the results were characterized false negative by the culture method.

What is claimed is:

1. A nucleic acid molecule for the detection and identification of Salmonella serotypes comprising a single stranded DNA fragment consisting of at least about 15 bases said single-stranded DNA fragment having a nucleotide sequence selected from the group consisting of: SEQ. ID No: 1; DNA sequences complementary thereto; and corresponding RNA or PNA sequences which hybridize to DNA or RNA of one or more of said Salmonella serotypes.

2. The nucleic acid molecule according to claim 1 comprising at least one of the following sequences:

| ST2  | TACTGAGTAT | GGCGGCAATC | ATCG     | (SEQ ID NO:2)  |
|------|------------|------------|----------|----------------|
| ST3  | AGGACCCCGA | TTTACCGCCC | T        | (SEQ ID NO:3)  |
| ST4  | AAGTTGTGTA | TCCATCTAGC | CAACC    | (SEQ ID NO:4)  |
| ST6  | CAGCGAGGTG | AAAACGACAA | AGGGG    | (SEQ ID NO:5)  |
| ST7  | GGCGATAGAT | TGTTTGTTGG | CTTCCT   | (SEQ ID NO:6)  |
| ST9  | ACAGGGTTTC | TCCGTTATCT | TTCTACGC | (SEQ ID NO:7)  |
| ST11 | AGCCAACCAT | TGCTAAATTG | GCGCA    | (SEQ ID NO:8)  |
| ST14 | TTTGCGACTA | TCAGGTTACC | GTGG     | (SEQ ID NO:9)  |
| ST15 | GGTAGAAATT | CCCAGCGGGT | ACTG     | (SEQ ID NO:10) |
| ST17 | GCGTCAGATA | TTATTGAATA | TCC      | (SEQ ID NO:11) |
| ST21 | GGGAGGATAC | GATGTAGTAC | ATGCGC   | (SEQ ID NO:12) |
| ST22 | TTACCCTGAC | AGCCGTTAGA | TATTCTC  | (SEQ ID NO:13) | and DNA sequences complementary thereto, corresponding RNA or PNA sequences, or fragments of the foregoing.

3. A nucleic acid molecule comprising at least one of the following sequences:

| ST1 TTACCCTGAC | AGCCGTAGAT | ATCTC | (SEQ ID NO:14) |
| ST5 CCGCTACTCC | GCCCTAATCC | ACAT  | (SEQ ID NO:15) |
| ST8 CGGCTTCAGG | CTTTCTCTTA | TTGGC | (SEQ ID NO:16) | and DNA sequences complementary thereto or corresponding RNA or PNA sequences thereof which hybridize selectively to DNA or RNA of one or more Salmonella serotypes.

4. A nucleic acid molecule according to any one of claims 1, 2 or 3 wherein the nucleic acid molecule additionally comprises a region of hybridising or non-hybridising DNA for labelling and/or binding to a solid support.

5. A method of detecting one or more Salmonella serotypes, said method comprising the step of providing at least one nucleic acid molecule according to claim 1 as a probe or primer in a DNA-based detection system.

6. A method as claimed in claim 5 wherein the DNA-detection system employs an amplification system selected from the group consisting of Polymerase Chain Reaction (PCR), Self-Sustained Sequence Replication (3SR), Q-beta Replicase Amplification System, the Ligase Amplification Reaction (LAR), Detection of Immobilized and Amplified Nucleic Acid (DIANA) and solid phase capture by hybridization probes.

7. A method as claimed in claim 6 wherein the amplification system is PCR.

8. A method as claimed in claim 7 wherein at least two oligonucleotide primers are employed and these are complementary to opposing strands of the nucleic acid of Salmonella serotypes.

9. A method as claimed in claim 8 wherein the primers are selected from the group consisting of the pairs ST11/ST14 and ST11/ST15 wherein the primers of each pair are complementary to opposing strands of the DNA.

10. A method as claimed in any one of claims 7 to 9 wherein nested primers are employed.

11. A method as claimed in claim 5 wherein nucleic acid molecule ST15 having the following sequence:

ST15 GGTAGAAATT CCCAGCGGGT ACTG (SEQ ID NO: 10)

or a DNA sequence complementary thereto, or corresponding RNA or PNA sequence is employed as the probe.

12. A method as claimed in claim 5 wherein *Salmonella Typhimurium* is detected.

13. A method as claimed in claim 12 wherein a nucleic acid molecule ST22 having the following sequence:

ST22 TTACCCTGAC AGCCGTTAGA TAT7CTC (SEQ ID NO: 13)

or a DNA sequence complementary thereto, or corresponding RNA or PNA sequence, is employed as the probe.

14. A kit for use in detecting Salmonella serotpes employing the PCR technique, comprising at least the following components:

a) a polymearase;

b) at least two oligonucleotide primers wherein the oligonucleotides are selected from the sequence in claim 1.

15. A kit for use in detecting Salmonella serotypes employing the Detection of Immobilized and Amplified Nucleic Acid (DIANA) technique, comprising at least the following components:

a) a polymerase;

b) at least two oligonucleotide primers wherein the oligonucleotides are selected from the sequence in claim 1 and provided with means for immobilisation and means for labelling.

16. A kit for use in detecting Salmonella serotypes employing the 3SR technique, comprising at least the following components:

a) a reverse transcriptase;

b) at least two oligonucleotide primers wherein the oligonucleotides are selected from the sequence in claim 1 and both primers have a polymerase binding site.

17. A kit for use in detecting Salmonella serotypes employing the LAR technique, comprising at least the following components:

a) a ligase;

b) at least two oligonucleotide primers wherein the oligonucleotides are selected from the sequence in claim 1 and are adjacent to each other in the sequence of claim 1.

18. A kit for use in detecting Salmonella serotypes employing the Q-beta replicase amplification technique, comprising at least the following components:

a) an RNA directed RNA polymerase;

b) an RNA probe with a 5'-MDV-1 structure or fragment thereof;

c) at least one oligonucleotide primer wherein the oligonucleotide is selected from the sequence in claim 1 and the primer is immobilised or permitting immobilisation.

19. A nucleic acid molecule for detection and identification of Salmonella serotypes comprising a single stranded DNA fragment consisting of a sequence, having about 15 to about 36 consecutive nucleotides selected from the group consisting of; Sequence ID No: 1; DNA sequences complementary thereto; and corresponding RNA or PNA sequences, wherein said nucleic acid is capable of hydridising to DNA or RNA of one or more of said Salmonella serotypes.

20. A nucleic acid molecule according to claim 19 consisting of a nucleotide sequence selected from the group consisting of:

| | | | | |
|---|---|---|---|---|
| ST2 | TACTGAGTAT | GGCGGCAATC | ATCG | (SEQ ID NO:2) |
| ST3 | AGGACCCCGA | TTTACCGCCC | T | (SEQ ID NO:3) |

-continued

| | | | | |
|---|---|---|---|---|
| ST4 | AAGTTGTGTA | TCCATCTAGC | CAACC | (SEQ ID NO:4) |
| ST6 | CAGCGAGGTG | AAAACGACAA | AGGGG | (SEQ ID NO:5) |
| ST7 | GGCGATAGAT | TGTTTGTTGG | CTTCCT | (SEQ ID NO:6) |
| ST9 | ACAGGGTTTC | TCCGTTATCT | TTCTACGC | (SEQ ID NO:7) |
| ST11 | AGCCAACCAT | TGCTAAATTG | GCGCA | (SEQ ID NO:8) |
| ST14 | TTTGCGACTA | TCAGGTTACC | GTGG | (SEQ ID NO:9) |
| ST15 | GGTAGAAATT | CCCAGCGGGT | ACTG | (SEQ ID NO:10) |
| ST17 | GCGTCAGATA | TTATTGAATA | TCC | (SEQ ID NO:11) |
| ST21 | GGGAGGATAC | GATGTAGTAC | ATGCGC | (SEQ ID NO:12) |
| ST22 | TTACCCTGAC | AGCCGTTAGA | TATTCTC | (SEQ ID NO:13) | and DNA sequences complementary thereto and corresponding RNA or PNA sequences.

21. The nucleic acid of claim 19, comprising a single-stranded DNA fragment having about 20 consecutive nucleotides.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 1972 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GATCGTGGCT GTAGCCTAAA AAGAGCCCGG CAGTATAATC ACCCCGGTCT GCAGCCGGGT      60
GCCCATAAAG GGCATTTAAG GATGGTTGAA ATATACCTGC ATCATCATTC GCCACTGAAA     120
TAGCAAGGCT ACTGGCATTG GCCATTGTGG TCGTACTGAG TATGGCGGCA ATCATCGTTG     180
CGCAATAGCT GTATTTGTTC ACTTTTTACC CCTGAATATG AAAGTGAATA CTCTTATTTT     240
TACAAAGTAA TAAGCACAGC AGCATGATGC GCAGTGCCTA TTAAACCTTT AAATATAACT     300
AAACTCCTGC CAGCAGCGAG TCATTGAGAG GATACGTTGC CTTAATGTTG AAAAATGGTG     360
GAAATTATTG GCTTCACGAT TATGCATATA ATACGATGTT TTTTGGTATC AATATGAATA     480
TTTTTACCGT GATAGTGTTG TCTTTAATGA TGAGAATATC TAACGGCTGT CAGGGTAATA     600
TAACCAAATT ATTGCTATCT GAATTATTAG GGCAGTTATT ATTAAGGAAG AAAAAGCTGA     660
ACAAGACCAT TAATTTGCTA AAATTACTGC CCGTAGTATT ATTAAGCGCA TGTACTACAT     720
CGTATCCTCC CCAGGATACA ACATCGGCAC CCGAGTTACC CCATCGTAAC GTACTCGTTC     780
AGCAACCTGA TAACTGTAGC GTTGGCTGTC CTCAAGGAGG AAGCCAACAA ACAATCTATC     840
GCCATGTCTA TACGCTCAAT AATAATAGCG TCACGAAATT TGCCAACTGG GTTGCCTATA     900
```

```
GCGTGACAAA AACCAGCCAG GCAAGCGGTC GCCCGCGAAC TGGGCGCAGG ACCCCGATTT      960

ACCGCCCTCG GATACGTTGG CCCCTTCCGC CTATAAAAAT GCCCATACGC TATTAAAAGT     1020

CGACAGGGGG CACCAGGCGC CGTTGGCAGG ATTGGGCGGC GTATCGGACT GGCCGTCGTT     1080

AAATTATTTA TCGAATATTA CGCCGCAGAA ATCCGCCCTG AATCAGGGAG CATGGGCTGC     1140

ACTGGAAAAC CGGGTGCGCG AACTTGCCAA ACAGGCTGAT GTATCTGTAG TGCACGTAGT     1200

GACCGGCCCC CTTTTTGAGC GCATATCGCC ACATTGCCAG AAGATGCGAC GGTAGAAATT     1260

CCCAGCGGGT ACTGGAAGGT TTTATTCACC GGAATGGCGC CGTCAAAAAG TGAAGGAAAT     1320

TACGCTGCAT TTATTATGGA TCAGAATACG CCCCGTTCGG CGAATTTTTG CGACTATCAG     1380

GTTACCGTGG AGGCTATCGA ACATAAAGCG AAGCCAGTGC TGACGCTGTG GTCTGCTTTG     1440

CCTGAAGCGG TAGCCAGCGA GGTGAAAACG ACAAAGGGGA GTCTGGCGCA GAAGTTAGGT     1500

TGTCGATGAG AAGCGCTATA CGGCGCGTAG AAAGATAACG GAGAAACCCT GTCAAGGGTC     1560

TTGATTTGCT ATAGAGTGAT GCAATCTCCC TTTTTTTAGT GTTACCATCA TCATGCCGGA     1620

CGAAGATAGC GATTTTCGTC TGTGTCGAAG GTTGTGCGCC AATTTAGCAA TGGTTGGCTA     1680

GATGGATACA CAACTTACTG TCAATAAATT CATTTTCTCT TTGTATGTGA TCTTGCGTAA     1740

TAAGTACAAT CCTTCATTCA CATCCATTCT CGTTCGTTTA AACCTGTTTC ACCAGTTCCG     1800

CGTCATTACT GGTAATAGCG GATATATATG TTTCATACCG TTTTACATTG ATCCCTTTCG     1860

CGCCGTAAGA TGTACGTACC TAATCTAACT TAAGCAGGGA ACTGTCATTC ATAACACAGA     1920

GTTTATTGGT ATCAATGGTA GATTATATTA CGGTGACAAT CTCGGGATGA TC           1972

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:2:

TACTGAGTAT GGCGGCAATC ATCG                                             24

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

AGGACCCCGA TTTACCGCCC T                                                21

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

AAGTTGTGTA TCCATCTAGC CAACC                                            25

(2) INFORMATION FOR SEQ ID NO:5:

(i) SEQUENCE CHARACTERISTICS:
        (A) LENGTH: 25 base pairs
        (B) TYPE: nucleic acid
```

(C) STRANDEDNESS: single
            (D) TOPOLOGY: linear (xi) SEQUENCE DESCRIPTION: SEQ ID NO:5:

CAGCGAGGTG AAAACGACAA AGGGG                                                       25

(2) INFORMATION FOR SEQ ID NO:6:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:6:

GGCGATAGAT TGTTTGTTGG CTTCCT                                                      26

(2) INFORMATION FOR SEQ ID NO:7:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:7:

ACAGGGTTTC TCCGTTATCT TTCTACGC                                                    28

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:8:

AGCCAACCAT TGCTAAATTG GCGCA                                                       25

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:9:

TTTGCGACTA TCAGGTTACC GTGG                                                        24

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:10:

GGTAGAAATT CCCAGCGGGT ACTG                                                        24

(2) INFORMATION FOR SEQ ID NO:11:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:11:

GCGTCAGATA TTATTGAATA TCC                                              23

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:12:

GGGAGGATAC GATGTAGTAC ATGCGC                                           26

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:13:

TTACCCTGAC AGCCGTTAGA TATTCTC                                          27

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:14:

TTACCCTGAC AGCCGTAGAT ATCTC                                            25

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

CCGCTACTCC GCCCTAATCC ACAT                                             24

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

CGGCTTCAGG CTTTCTCTTA TTGGC                                            25

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:17:

```
AATTTAATAC GACTCACTAT AGGGATC                                                     27

(2) INFORMATION FOR SEQ ID NO:18:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (xi) SEQUENCE DESCRIPTION: SEQ ID NO:18:

AATTTAATAC GACTCACTAT AGGGA                                                       25

(2) INFORMATION FOR SEQ ID NO:19:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:19:

CAGTACCCGC TGGGAATTTC TAC                                                         23

(2) INFORMATION FOR SEQ ID NO:20:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (xi) SEQUENCE DESCRIPTION: SEQ ID NO:20:

CGACGGTAGA AATTCCCAGC GGGTACTGGA AGGTTTTATT CACCG                                  45

(2) INFORMATION FOR SEQ ID NO:21:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (xi) SEQUENCE DESCRIPTION: SEQ ID NO:21:

GTTCGGCGAA TTTTTGCGAC TATCAGGTTA CCGTGGAGGC TATCG                                  45

(2) INFORMATION FOR SEQ ID NO:22:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (xi) SEQUENCE DESCRIPTION: SEQ ID NO:22:

TCGAAGGTTG TGCGCCAATT TAGCAATGGT TGGCTAGATG GATAC                                  45

(2) INFORMATION FOR SEQ ID NO:23:

(i) SEQUENCE CHARACTERISTICS:
         (A) LENGTH: 50 base pairs
         (B) TYPE: nucleic acid
         (C) STRANDEDNESS: single
         (D) TOPOLOGY: linear
```

-continued (xi) SEQUENCE DESCRIPTION: SEQ ID NO:23:

TTATATTACC CTGACAGCCG TTAGATATTC TCATCATTAA AGACAACACT 50